United States Patent [19]

Bogdanov et al.

[11] Patent Number: 5,605,672
[45] Date of Patent: Feb. 25, 1997

[54] BLOOD POOL IMAGING COMPOSITION AND METHOD OF ITS USE

[75] Inventors: Alexei A. Bogdanov, Newton; Ralph Weissleder, Charlestown; Thomas J. Brady, Winchester; Ronald Callahan, Boston, all of Mass.

[73] Assignee: The General Hospital Corporation, Boston, Mass.

[21] Appl. No.: 74,319

[22] Filed: Jun. 9, 1993

[51] Int. Cl.$^6$ .............................. A61K 51/00; C07F 5/00
[52] U.S. Cl. ....................... 424/1.65; 424/1.69; 424/1.77; 534/16
[58] Field of Search .................................. 424/1.65, 1.69, 424/1.77; 534/16

[56] References Cited

U.S. PATENT DOCUMENTS

| | | | |
|---|---|---|---|
| 4,647,447 | 3/1987 | Gries et al. | 424/9 |
| 4,707,352 | 11/1987 | Staurianopolous | 424/1.53 X |
| 4,849,208 | 7/1989 | Stavrianopoulos | 424/1.53 X |
| 4,855,353 | 8/1989 | Kurami et al. | 525/54.1 |
| 4,877,868 | 10/1989 | Reno et al. | 530/390 |
| 4,951,675 | 8/1990 | Groman et al. | 128/653.4 |
| 5,057,313 | 10/1991 | Shih et al. | 424/85.91 |
| 5,069,216 | 12/1991 | Groman et al. | 128/653.4 |
| 5,094,848 | 3/1992 | Brixner | 424/1.53 X |
| 5,141,739 | 8/1992 | Jung et al. | 424/4 |
| 5,160,725 | 11/1992 | Pilgrimm | 424/9 |
| 5,164,176 | 11/1992 | Gustavson et al. | 424/1.49 |
| 5,171,563 | 12/1992 | Abrams et al. | 424/1.45 |
| 5,208,324 | 5/1993 | Klaveness et al. | 424/9 |
| 5,213,788 | 5/1993 | Ranney | 424/9 |
| 5,250,666 | 10/1993 | Gustavson et al. | 530/391.5 |
| 5,328,992 | 7/1994 | Peter et al. | 534/16 |
| 5,382,654 | 1/1995 | Tyle et al. | 530/311 |

FOREIGN PATENT DOCUMENTS

| | | |
|---|---|---|
| 0300969 | 7/1988 | European Pat. Off. . |
| WO90/12050 | 10/1990 | European Pat. Off. . |
| PCT/US94/06282 | 5/1995 | European Pat. Off. . |
| WO91/15753 | 10/1991 | WIPO . |
| WO91/18630 | 12/1991 | WIPO . |
| 94/06282 | 9/1994 | WIPO . |

OTHER PUBLICATIONS

Sawhney et al., Biomaterials 13(12) 1992, pp. 863–870 as Abstracted in Chemical Abstracts AN 118:11690 See Abstract.
Klibanov et al., Am. J. Physiol, 261 (4, suppl), pp. 60–65 as Abstracted in Chemical Abstracts AN 115:239558, See Abstract.
Pimm et al., EP. Jour. Nuc. Med., *Scintigraphic evaluation of the pharmacokinetics of a soluble polymeric drug carrier,* Jun., 1992.
Zanelli, Nuclear Medicine, *The Preparation of kits for labelling macromolecules of biological interest with technetium–99m,* 1987.
Abuchowski et al., J. Biol. Chem., 252:3578–81 (1977).
Abuchowski et al., Bioch. Biophy. Acta., 578:41–46 (1979).
Abuchowski et al., J. Biol. Chem., 252:3582–86 (1977).
Abuchowski and Davis, "Soluble Polymer–Enzyme Adducts," Ch. 13, *Enzymes as Drugs,* (Wiley, New York 1981).
Beauchamp et al., Anal. Biochem., 131:25–33 (1983).

(List continued on next page.)

*Primary Examiner*—Cynthia Harris-Kelly
*Attorney, Agent, or Firm*—Fish & Richardson P.C.

[57] ABSTRACT

The invention features a method of blood pool imaging which utilizes an imaging agent which can be easily labelled with a radioactive isotope and injected into a patient. The imaging agent is a covalent conjugate of a polymeric carrier, protective groups, and chelating groups. The imaging agent is preferably provided in the form of a blood pool imaging composition, which includes an imaging agent of the invention, a buffer and a reducing compound. A radioactive isotope is added to the blood pool imaging composition to label the imaging agent, and the composition containing the labelled imaging agent is injected intravenously into a patient.

44 Claims, 4 Drawing Sheets

OTHER PUBLICATIONS

Chazov et al., *Thromb. Res.*, 12, 809–816 (1978).
Chung–Ja et al., *Anal. Biochem.*, 165:114–127 (1987).
Duewell et al., *Invest. Radiol.*, 26:50–57 (1991).
Fujimoto et al., *Cancer*, 56:2404–2410 (1985).
Kennady et al., *Am. Surg.*, 33:763–771 (1967).
Manabe et al., *Biochem. Biophys. Acta*, 883:460–67 (1986).
Schmiedl, et al., *Invest. Radiol.*, 26:65–70 (1991).
Schumann–Giampieri et al., *Invest. Radiol.*, 26:969–974 (1991).
Torchilin et al., *J. Biomed. Mater. Res.*, 11:223–234 (1977).
Torchilin et al., *J. Biom. Mater. Res.*, 19:461–466 (1985).
Winding, O., *Neuroradiol.*, 21:123–126 (1981).
Wright et al., *Radiology*, 142:351–54 (1982).

BLOOD POOL IMAGING COMPOSITION AND METHOD OF ITS USE

This invention was made with Government support under Contract #RO1-CA-54886 awarded by the National Institutes of Health. The Government has certain rights in the invention.

BACKGROUND OF THE INVENTION

The present invention relates to blood pool imaging by nuclear medicine techniques.

Nuclear blood pool imaging, i.e., the imaging of radioactively labelled blood to allow visualization of a blood pool, is a well established diagnostic clinical tool. Common applications for blood pool imaging are the determination of heart function after myocardial infarction, and bleeding studies, i.e., the detection of occult bleeding sites, typically in the gastro-intestinal tract.

Blood pool imaging is performed by labelling red blood cells of a patient with a radioactive isotope, e.g., 99 mTc pertechnetate. Some blood labelling procedures require the removal of blood from the patient for in vitro labelling, after which the labelled blood is reintroduced to the patient. Accordingly, such procedures are relatively time-consuming, and carry with them risks inherent in blood handling, e.g., the transmission of infectious diseases by injecting the labelled blood into the wrong patient. Other imaging procedures involve labelling of red blood cells in vivo, but these procedures typically result in labelling efficiencies of less than 85%. In addition, all of these procedures require at least 20 to 30 minutes of preparation time per patient.

SUMMARY OF THE INVENTION

The invention features blood pool imaging compositions which eliminate the need to handle and label blood products. The new compositions contain an imaging agent which can be easily labelled with a radioactive isotope and injected into a patient. The imaging agent comprises a covalent conjugate of a polymeric carrier with protective groups and chelating groups. The imaging agent preferably comprises an amino acid backbone conjugated with polyethylene glycol protective groups and acetic acid derivative chelating groups, more preferably the backbone is poly-1-lysine conjugated with a monomethoxy ether of polyethylene glycol-O-succinate and with diethylenetriamine pentaacetic acid.

The blood pool imaging composition includes an imaging agent of the invention, a buffer, and a reducing compound. When a radioactive isotope is added to the blood pool imaging composition to label the imaging agent, the reducing compound advantageously reduces the oxidation state of the radioactive isotope to a state which readily binds to the chelating groups of the imaging agent. In this oxidation state, the isotope rapidly binds to the imaging agent, and the resulting labelled imaging agent provides excellent blood pool imaging when injected intravenously into a patient. The buffer maintains the pH of the compositions at a physiologically acceptable level.

The compositions of the invention are particularly suited for labelling with technetium, an isotope which is advantageous for use in blood pool imaging applications. Technetium, as typically supplied, does not bind to chelating agents. Significantly, the compositions of the invention can be easily and rapidly labelled with technetium, without requiring purification of the technetium.

The blood pool imaging composition may be in the form of a solution, or may be freeze-dried and lyophilized to form a powder. Preferably, the blood pool imaging composition has a pH of from about 4 to 6, more preferably about 5.1 to 5.2.

In another aspect, the invention features a method of imaging a blood pool in a patient. The method includes providing a blood pool imaging composition comprising a radiolabelled imaging agent of the invention, a reducing compound, and a buffer, and introducing the blood pool imaging composition into the patient's bloodstream.

In yet another aspect, the invention features a method of preparing a blood pool imaging composition of the invention. The method includes preparing a buffer solution, dissolving the new imaging agent in the buffer solution, and adding a reducing compound to the solution. Preferably, the buffer solution has a pH of about 9 to 11, and a sufficient quantity of the reducing compound solubilized in acid is added to bring the pH of the solution to about 4 to 6. Preferably, the buffer solution is substantially oxygen-free, i.e., contains no appreciable dissolved oxygen from the air, and the molar ratio of the reducing compound to the imaging agent is preferably from 20:1 to 100:1.

The term "protective group", as used herein, refers to a molecule which prevents a backbone molecule and a chelating group from extensive linking of water to their chains which could inhibit contact with other macromolecules.

The term "chelating group" as used herein, refers to one or more molecules, or chemical radicals, or moieties, which provide a favorable environment for linking a cation. Dissociation of the cation from the environment is hindered due to kinetic or/and thermodynamic stability of linking to the chelating group.

The verb "label" as used herein, refers to binding of a radioactive isotope or a cation including the isotope to a chelating group of the imaging agent by chelation.

The term "derivative" as used herein mean a compound whose core structure is the same as, or closely resembles that of a parent compound, but which has a chemical or physical modification, such as different or additional side groups; the term includes copolymers of parent compounds that can be linked to other atoms or molecules.

Other features and advantages of the invention will be apparent from the following description of the preferred embodiments and from the claims.

DESCRIPTION OF THE PREFERRED EMBODIMENTS

Preferred imaging agents include a polymeric backbone having amino groups which are covalently bonded to chelating and protective groups. It is preferred that from about 25 to 30% of the amino groups of the backbone are covalently linked with protective groups, and the remaining amino groups are covalently linked with chelating groups.

Preferred backbones include polyamino acids, polyethyleneimines, natural saccharides, aminated polysaccharides, aminated oligosaccharides, polyamidoamine, polyacrylic acids, and polyalcohols.

Preferred polyamino acids have 20–560 amino acid residues, more preferably 150 to 250 amino acid residues, a molecular weight of 1,000–100,000 daltons, and are preferably non-proteinaceous. The polyamino acid may be a polymer of a single species, or at least two different species of amino acid, or may be a block copolymer. The polyamino acid may include polyamino acid fragments linked by cleavable bonds, e.g., S—S bonds. In particular, the polyamino acid may be, e.g., poly-1-lysine, poly-d-lysine, poly-alpha, beta-(2-aminoethyl)-D,L aspartamide, or poly-1-aspartic acid. Preferably, the backbone is a polylysine, more preferably poly-1-lysine, having a molecular weight of from about 25 to 30 kD.

The polymeric backbones preferably contain peptide bonds. The same bonds are involved in conjugating chelating groups with the amino groups of the backbone. The imaging agents, therefore, are potentially biodegradable by various animal non-specific peptidases. To assist in vivo elimination of the imaging agent, elements of the polymeric backbone or the protective groups or chelating groups could be linked together by a semistable linkage, such as S—S bonds. Small amounts of trapped compositions may be removed from the body by degradation to smaller fragments. However, a variety of activated PEG derivatives may be used for the preparation of the imaging agent thus making them either virtually nondegradable.

Suitable compounds for use as chelating groups include those which bind cations of transitional elements and lanthanides. Preferred chelating agents are those which bind cations of technetium, e.g., 99 mTc pertechnetate, and/or cations of indium, e.g., (III)In. Chelating groups which bind technetium include, diethylenetriamine-pentaacetic acid (DTPA), mercaptoacetyltriglycine, ethylenedecysteine, 1-emine-3-mercaptobutace, and bis (aminoethanethiol) carboxylic acid. Other chelating groups include triethylenetetramine-hexaacetic acid, ethylenediamine-tetraacetic acid (EDTA), 1,2-diaminocyclohexane-N,N,N', N'-tetra-acetic acid, N,N'-di(2-hydroxybenzyl) ethylenediamine, N-(2-hydroxy-ethyl)ethylenediaminetriacetic acid, nitrilotriacetic acid, ethylene-bis(oxyethylene-nitrilo) tetraacetic acid, 1,4,7,10-tetraazacyclodo-decane-N,N',N'',N'''-tetraacetic acid, 1,4,7,10-tetraaza-cyclododecane-N,N',N''-triacetic acid, 1,4,7-tris(carboxymethyl)-10-(2'-hydroxy-propyl)-1,4,7,10-tetraazocyclodecane, 1,4,7-triazacyclonane-N,N',N''-triacetic acid, or 1,4,8,11-tetraazacyclotetra-decane-N,N',N'',N'''-tetra-acetic acid. Some preferred chelating groups may contain phosphorus or boron atoms.

Preferred protective groups are polyethylene glycol (PEG) derivatives. Preferred protective groups include from 17 to 220, more preferably 45 to 100 (OCH$_2$CH$_2$) groups. The protective groups may be, e.g., polyethylene glycol, methoxypolyethylene glycol, methoxypolypropylene glycol, a copolymer of polyethylene glycol, methoxypolyethylene glycol, or methoxypolypropylene glycol, or derivatives thereof. In addition, the protective groups may be a block copolymer of polyethylene glycol and one of the group of polyamino acids, polysaccharides, polyamidoamines, polyethyleneamines, or polynucleotides. The protective group may also be a copolymer of polyethylene glycol including a monoester of a dicarboxylic acid. The protective group preferably has a molecular weight of 500–10,000 daltons.

Imaging agents of the invention may thus have the formula:

wherein the groups can be linked in any order, e.g., the $R_1$ unit can be repeated several times in the chain before an $R_2$ unit occurs, and vice versa; wherein k is 10–560; $R_1$ is $(CH_2)_4NHCO(CH_2)_nCOOCH_2CH_2A$—B—$OR_3$ where n=0–8, $R_3$=H, $(CH_2)_pCH_3$ or $(CH_2)_pCOOH$, where p=0–7, A=$[OCH_2CH_2]_x$, where x is 15–220, and B=$[OCH_2CH_2]_x$ or $[OCH(CH_3)CH_2]_y$, where y+x is 10–220; and $R_2$ is $(CH_2)_4$—$R_4$, where $R_4$ is a chelating group.

Imaging agents suitable for use in the invention may be synthesized using the procedures described in copending U.S. Ser. No. 07/940,590, the disclosure of which is incorporated herein by reference. One preferred procedure is described below in Example 1.

The blood pool imaging composition of the invention is formed by mixing the imaging agent with a buffer solution and a reducing compound. The three components may be mixed using standard procedures known in the art. Preferably, the imaging agent is first dissolved in the buffer solution, after which the reducing compound is added thereto. One suitable method is described in Example 1.

Suitable buffer salts, for use in preparing the buffer solution, include salts of mono- or di-carboxylic acids, or 2-(N-morpholino) alkyl sulfonic acids. A preferred buffer salt is sodium acetate. Preferably, the buffer solution also contains sodium hydroxide to counteract a lowering pH. A preferred method for preparing the buffer solution is described in Example 1, below. Preferably, the buffer has a concentration of from about 0.1 to 0.2M. The imaging agent is preferably dissolved in the buffer solution at a concentration of from about 0.1 to 10 mg/ml, more preferably about 1 to 5 mg/ml.

Suitable reducing compounds include stannous (II) chloride or sodium dithionite. A preferred reducing compound is a solution of stannous (II) chloride in concentrated hydrochloric or acetic acid. The preferred solution has a molarity of from about 80 to 90 mM. The amount of reducing compound (in moles) added to the buffer/imaging agent solution is preferably less than or equal to the molar amount of chelating groups on the imaging agent. Most preferably, the molar ratio of reducing compound to chelating groups is approximately 0.5:1 to 2:1, more preferably about 0.9:1 to 1:1. The resulting pH of the solution after addition of the reducing compound is preferably from about 4 to 6, more preferably from about 5.1 to 5.2.

Preferably, the blood pool imaging composition includes a stabilizer, if the composition is to be stored over an extended period, e.g., more than 1 month. Any conventional, physiologically acceptable stabilizer may be used, e.g., sodium ascorbate, 1-methionine, p-aminobenzoic acid, sodium aminobenzoate, cysteine, sodium citrate, and mixtures thereof.

The blood pool imaging composition may be provided as a liquid solution, as described above, which is preferably stored in sterile vials, in an atmosphere of inert gas, e.g., argon. Preferably, the composition is stored at low temperature, more preferably less than or equal to −20° C. Alternatively, the composition may be subjected to freezing in dry ice and lyophilization, and stored as a dry powder in an atmosphere of inert gas. The dry powder typically can be stored at ambient temperature.

If the composition is supplied as a solution, the imaging agent is labelled by mixing the composition with a standard solution of a radioactive isotope. If the composition is supplied as a powder, the powder is preferably reconstituted in a sterile solution of the isotope in physiological saline (0.9% NaCl). Labelling typically is complete in about 3 minutes or less, after the isotope and blood pool imaging composition are mixed. The labelled composition may be stored for up to about 6 hours without decomposition, even if labelled to a radioactivity of 100 mCi/mg or higher.

Any conventional radioactive isotope from the transitional elements or lanthanides which will bond to the chelating groups may be used. As discussed above, the preferred blood pool imaging compositions are particularly useful for labelling with technetium. Technetium isotopes are also preferred for many applications, as they provide superior imaging quality and have a short half-life, providing low exposure. Preferred isotopes include 99 mTc pertechnetate, 99 mTc pyrophosphate, and 99 mTc glucarateo Such isotopes are commercially available from, for example, Syncor Int'l, (Chatsworth, Calif.), or from DuPont. A sufficient quantity of the isotope is used to achieve a radioactivity of 0.1–5 GBq (gigaBequerel) per mg of the imaging agent in the blood pool imaging composition.

The preferred volume and radioactivity of the labelled blood pool imaging composition to be injected into a particular patient will vary depending upon the imaging application (e.g., cardiography vs. bleeding studies), the body mass of the patient, and the sensitivity of the imaging apparatus to be used. Preferred volumes can be easily determined by the artisan, taking these factors into consideration. Typically, a volume having a radioactivity of from about 1 to 10 mCi (37 to 370 GBq) will be administered to a child, while a volume having a radioactivity of from about 1 to 20 mCi (37 to 740 GBq) will be administered to an adult. The volume needed to provide a given radioactivity can be determined using a Well Counter or other type of dose calibrator, as is known in the art.

EXAMPLE 1

A sodium acetate buffer was dissolved in sterile apyrogenic water at a concentration of 0.2M (16.5 g/l). The resulting buffer solution was brought to a pH of 10 by addition of 10N NaOH, boiled for 1 minute, and cooled to room temperature by passing a slow stream of nitrogen through it.

A PEG-poly-1-lysine-DTPA imaging agent was prepared as follows:

620 mg of poly-1-lysine (PL hydrobromide, MW 41,100, (Sigma Chemical Co., DP: 196 1-lysine residues, 25 mM epsilon-aminogroups of 1-lysine, hydrobromide) was dissolved in 112 ml of 0.1M carbonate buffer (pH 8.7). 2.9 g methoxy polyethylene glycolsuccinyl hydroxysuccimidyl ester (MPEGOSu, MW 5,200) was dissolved in 5 ml of dry DMSO. The MPEGOSu solution was added drop-wise to the PL solution under agitation and the mixture was incubated for 2 hours under stirring to form a MGEG-PL solution.

A suspension of cyclic anhydride of DTPA (0.5 g/ml in DMSO) was prepared by adding 200 µl portions (1.5 g of cDTPA total) to the MPEG-PL solution and adjusting the pH to 8 with 5N NaOH after each addition. (Alternatively, the solution may be prepared by mixing of 2.5 mmol of DTPA, 0.5 mmol N-hydroxysulfosuccinimide (pH 4) and 0.5 mmol ethyl diaminopropylcarbodiimide in 50 ml of water.) The solution was then mixed for 3 min and added to the mixture the MPEG-PL solution (pH 8). No titratable amino groups were detected at this point.

The reaction mixture was then diluted to 300 ml with 0.2M sodium citrate (pH 6), filtered through 0.45 µm nylon filter, and dialyzed in a flow-through cell using a membrane with a cut-off of 50 kD (for globular proteins). The product was then concentrated to 30–50 ml and diluted to 300 ml with citrate. This procedure was repeated twice using water instead of citrate at the last stage. Final purification was achieved by passing the solution through a DEAE-anion exchange resin. The product was collected as flow-through. The product was then filtered through a sterile 0.2 µm membrane, resulting in the final imaging agent.

This imaging agent was next dissolved in the buffer solution, at a concentration of 1 mg/ml.

The reducing compound, a 2% solution of stannous (II) chloride in concentrated hydrochloric acid, was then added to the buffer solution, at a volume ratio of 5 µl per ml. The resulting pH of the buffer was about 5.1.

To label the imaging agent in the blood pool imaging composition, the solution was mixed with an aqueous solution of 99 mTc pertechnetate. Labelling proceeded rapidly, with about 98% of the pertechnetate being reduced and tightly associated with chelating groups of the imaging agent in about 1 to 3 minutes.

EXAMPLE 2

Figure 1:
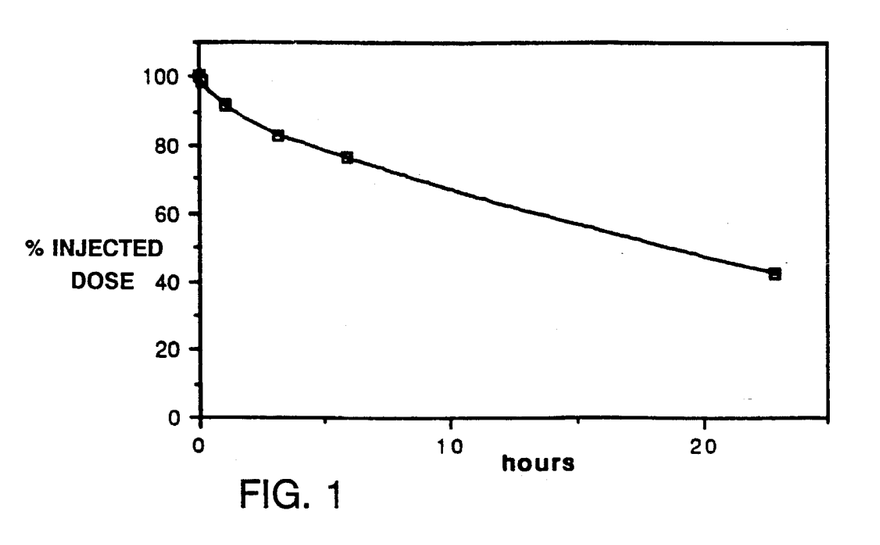
FIG. 1 is a graph of the blood clearance kinetics observed in rabbits injected with a blood pool imaging composition according to one embodiment of the invention.

Four New Zealand white rabbits were injected with 185 MBq (5 mCi) of the labelled blood pool imaging composition of Example 1, diluted in 1 ml of saline. The correct volume of solution required to provide 5 mCi radioactivity was determined using a Well Counter. Blood samples were drawn from the ear veins of the rabbits at 6 time intervals, and the radioactivity of each sample determined by gamma-counting, with results as shown in FIG. 1. In FIG. 1, the observed radioactivity of the injected sample was initially 100% of the radioactivity of the injected composition, and slowly declined to approximately 40% after about 20 hours. The data in FIG. 1 was corrected for decay.

EXAMPLE 3

Figure 2:
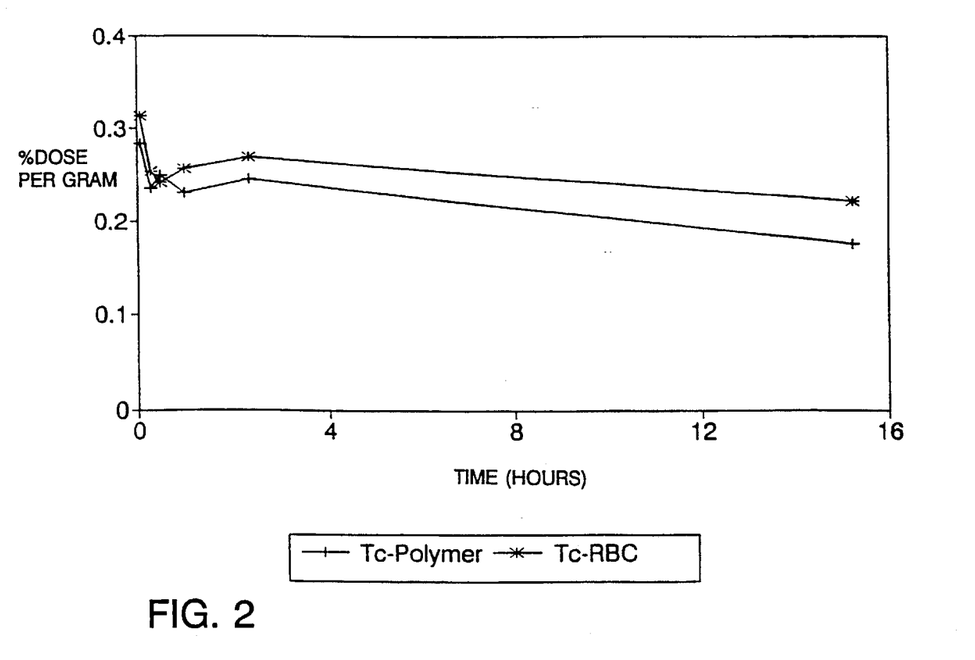
FIG. 2 is a graph of the comparative blood clearance kinetics observed in a Rhesus monkey injected with a blood pool imaging composition, and a Rhesus monkey injected with Technetium (Tc)-labelled red blood cells.
Figure 3:
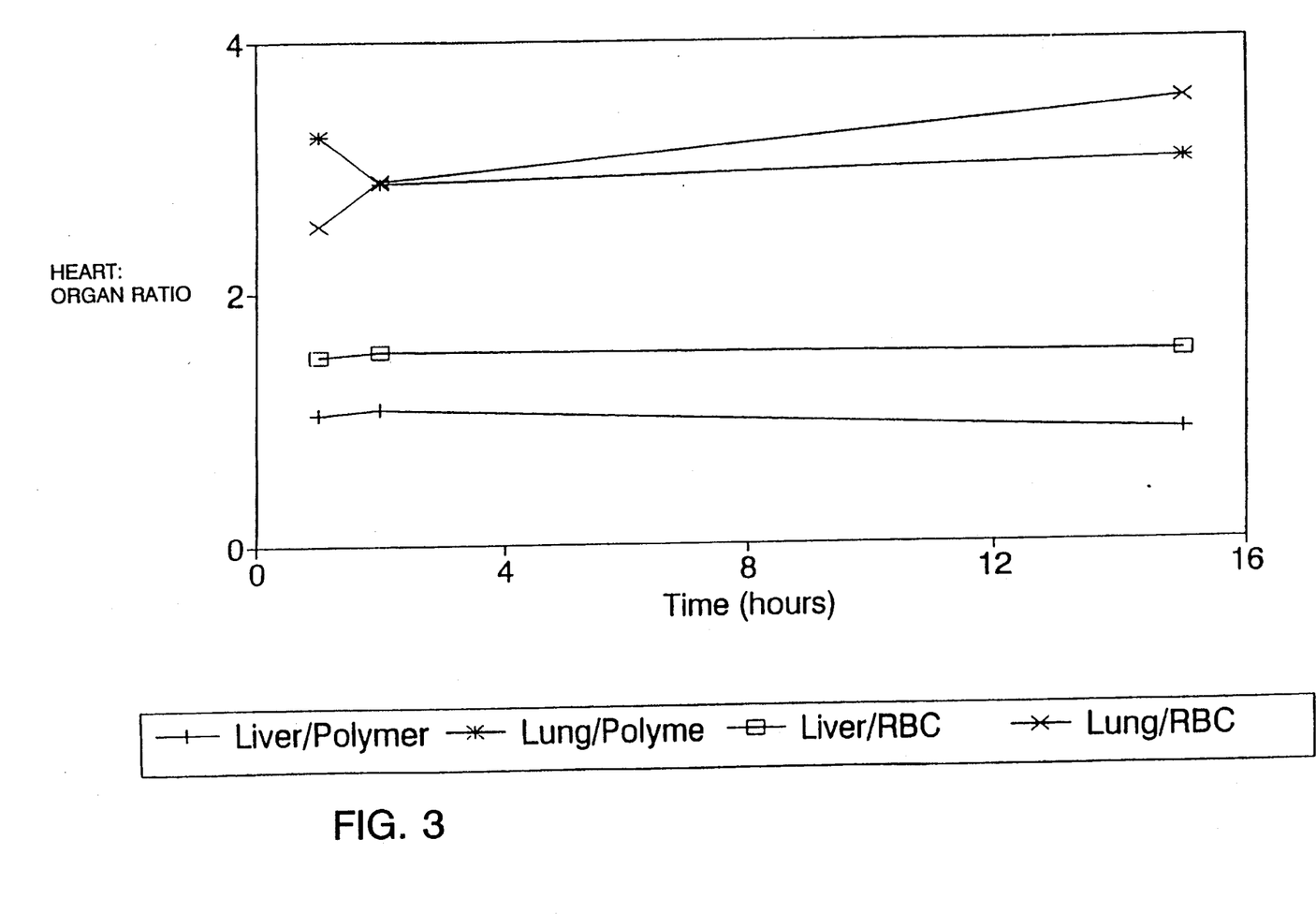
FIG. 3 is a graph of the heart:organ ratios of a Rhesus monkey injected with a blood pool imaging composition and a Rhesus monkey injected with Tc-labelled red blood cells.

A male Rhesus monkey was injected with 185 MBq of the labelled blood pool imaging composition of Example 1 (+). In a separate experiment, the same animal was injected with 185 MBq red blood cells labelled with Tc99m (*) (Tc99m-RBC). Blood samples were drawn at several time intervals after each injection, and the radioactivity of each sample was determined by gamma-counting, with results as shown in FIG. 2. As shown in FIG. 2, in both experiments the radioactivity (% dose per gram) initially declined sharply, and then remained relatively level for approximately 16 hours. As shown, the imaging composition of the invention gave results comparable to those obtained using Tc-labelled red blood cells. The data was corrected for decay.

EXAMPLE 4

A male Rhesus monkey was injected with 185 MBq of the labelled blood pool imaging composition of Example 1. In a separate experiment, one week later, the same animal was injected with 185 MBq red blood cells labelled with Tc99m (Tc99m-RBC). Heart:organ ratios were determined for each by measuring counts in the lung and in the liver by a gamma camera. The liver and lung ratios, respectively, for the composition of Example 1 are shown by the symbols "+" and "*" and for Tc-RBC, by the symbols "□" and "×".

EXAMPLE 5

Figure 4:
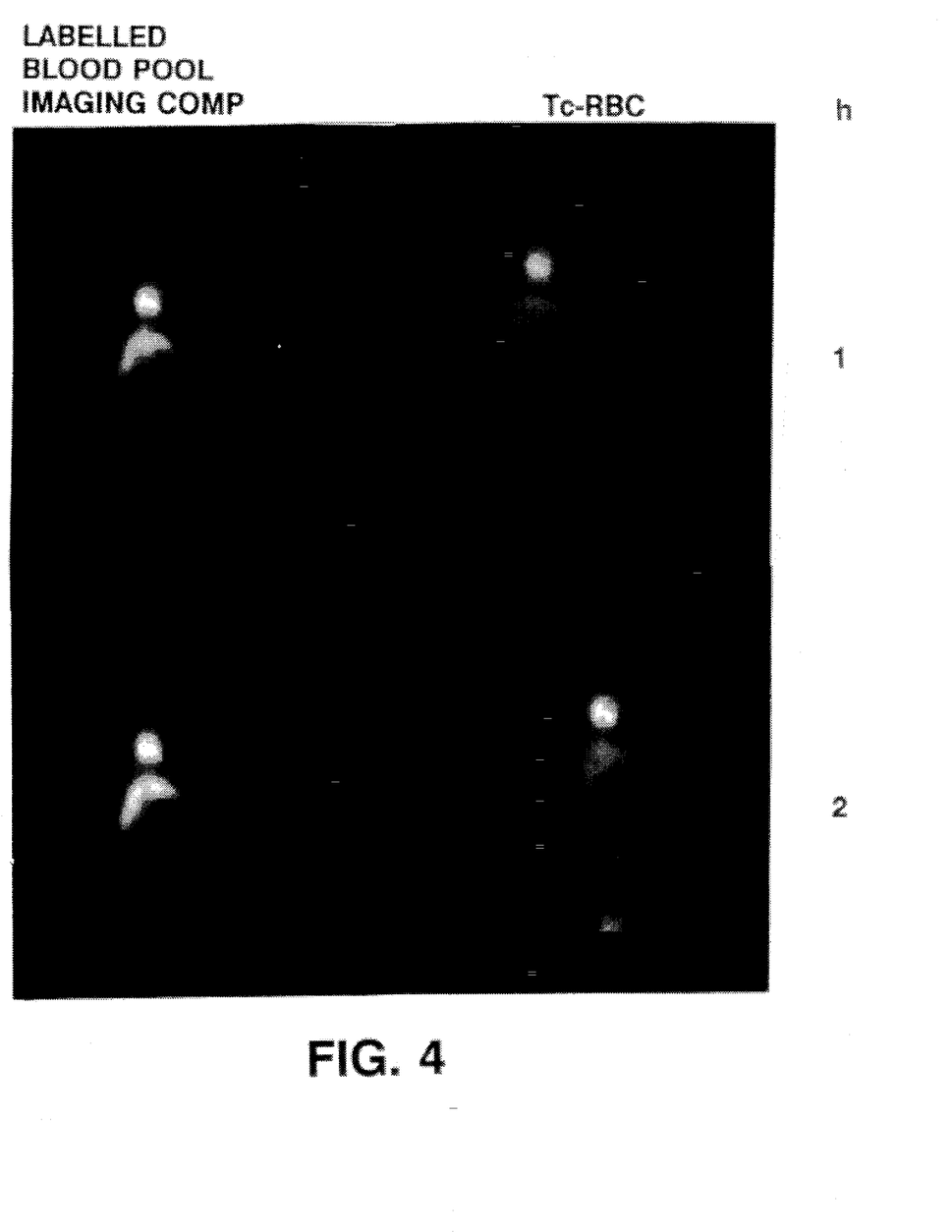
FIGS. 4 and 4a show gamma camera chest and abdomen images, respectively, of a Rhesus monkey injected with a blood pool imaging composition, and a Rhesus monkey injected with Tc-labelled red blood cells.
Figure 4A:
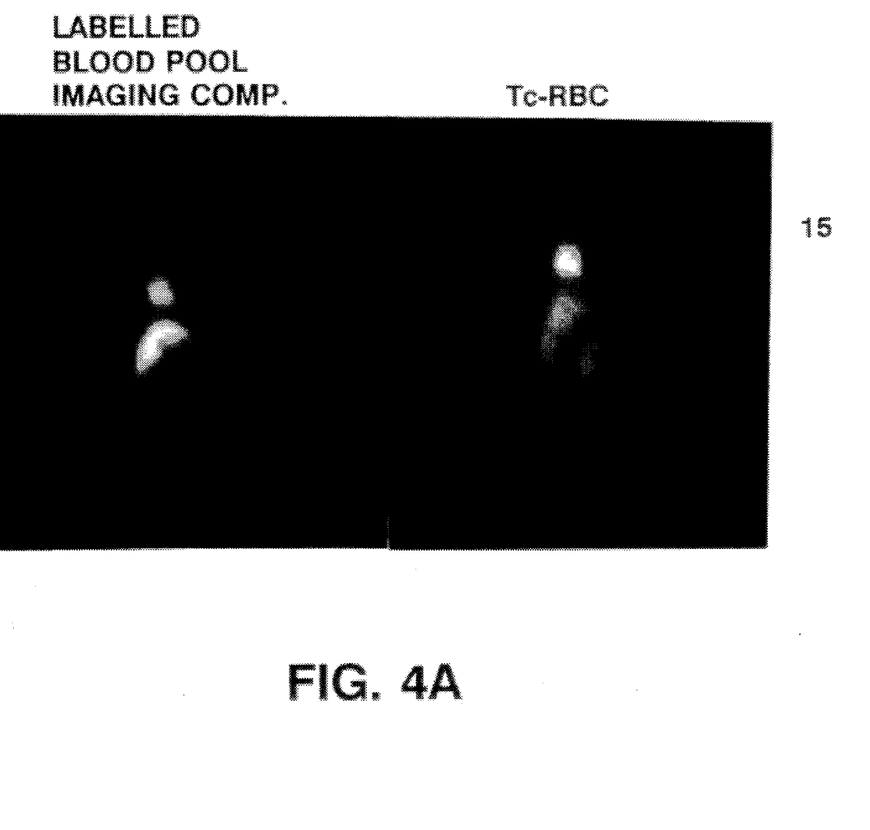

A male Rhesus monkey was injected with 185 MBq of the labelled blood pool imaging composition of Example 1. In a separate experiment, one week later, the same animal was injected with 185 MBq red blood cells labelled with Tc99m (Tc99m-RBC). Images were taken with a gamma camera of the chest and abdomen of the Rhesus monkey 1, 2 and 15 hours after each injection, as shown in FIG. 4.

As shown in FIGS. 1–4, a stable image was obtained immediately after injection with the blood pool imaging composition of Example 1, and the quality of the ventriculogram, i.e., the heart/liver and heart/lung ratios observed, remained constant for at least 3 to 6 hours post-injection. The figures also illustrate that the preferred labelled blood pool imaging compositions give heart/organ ratios very similar to ratios obtained using Tc-labelled red blood cells.

Other embodiments are within the claims.

We claim:

1. A blood pool imaging composition comprising:
   an imaging agent comprising a polymeric backbone, protective groups, and chelating groups, wherein each of said protective groups and chelating groups are, independently, covalently bonded to amino groups present on said backbone, and wherein said protective groups are polyethylene glycol derivatives, a reducing compound, and a buffer.

2. The composition of claim 1, wherein said polymeric backbone is a polyamino acid having 150 to 250 amino acid residues.

3. The composition of claim 2, wherein said polyamino acid is poly-1-lysine.

4. The composition of claim 1, wherein said protective groups comprise from 17 to 220 $(OCH_2CH_2)$ groups.

5. The composition of claim 4, wherein said protective groups comprise from 45 to 100 $(OCH_2CH_2)$ groups.

6. The composition of claim 1, wherein said derivative is a methoxypolyalkylene glycol.

7. The composition of claim 1, wherein said derivative is a polymer of polyethylene glycol monoesterified with a dicarboxylic acid.

8. The composition of claim 1, wherein said chelating group binds cations of transitional elements and lanthanides.

9. The composition of claim 8, wherein said chelating group binds cations of technetium.

10. The composition of claim 9, wherein said chelating group binds 99 mTc pertechnetate.

11. The composition of claim 8, wherein said chelating group binds cations of indium.

12. The composition of claim 8, wherein said chelating group is selected from the group consisting of diethylenetriaminepentaacetic acid, mercaptoacetyltriglycine, ethylenedicysteine, 1-imine-4-mercaptobutane, and bis(aminoethanethiol) carboxylic acid.

13. The composition of claim 1, wherein the chelating group contains phosphorus or boron.

14. The composition of claim 1, wherein said reducing compound is stannous (II) chloride or sodium dithionite.

15. The composition of claim 1, wherein the molar ratio of said reducing compound to said imaging agent is from 20:1 to 100:1.

16. The composition of claim 1, wherein said buffer comprises sodium acetate.

17. The composition of claim 1, further comprising a stabilizer.

18. The composition of claim 17, wherein said stabilizer is selected from the group consisting of sodium ascorbate, sodium aminobenzoate, cysteine, sodium citrate, and mixtures thereof.

19. The composition of claim 1 wherein said protective groups are bonded to said backbone with a non-biodegradable bond.

20. The composition of claim 1 wherein said protective groups are bonded to said backbone with a biodegradable bond.

21. The composition of claim 1, wherein said imaging agent is a compound having the formula:

wherein the groups can be linked in any order, wherein k is 10–560; $R_1$ is $(CH_2)_4NHCO(CH_2)_nCOOCH_2CH_2A—B—OR_3$ where n=0–8, $R_3$=H, $(CH_2)_pCH_3$ or $(CH_2)_pCOOH$, where p=0–7, A=$[OCH_2CH_2]_x$, where x is 15–220, and B=$[OCH_2CH_2]_x$ or $[OCH(CH_3)CH_2]_y$, where y+x is 10–220; and $R_2$ is $(CH_2)_4$—$R_4$, where $R_4$ is a chelating group.

22. A method of imaging a blood pool in a patient comprising the steps of:
   providing a blood pool imaging composition comprising a radiolabelled imaging agent which comprises a polymeric backbone, protective groups, and chelating groups, wherein each of the protective groups and chelating groups are, independently, covalently bonded to amino groups present on said backbone, and wherein said protective groups are polyethylene glycol derivatives; a reducing compound; and a buffer; and
   introducing the blood pool imaging composition into the patient's bloodstream.

23. A method of claim 22, wherein the blood pool imaging composition is prepared by dissolving the imaging agent in a buffer solution, and adding a reducing compound to the buffer solution.

24. A method of claim 23, wherein the buffer solution has a pH of about 9 to 11, and a sufficient quantity of the reducing compound solubilized in acid is added to bring the pH of the solution to about 4 to 6.

25. A method of claim 23, wherein the buffer solution is oxygen-free.

26. A method of claim 23, wherein the molar ratio of the reducing compound to the imaging agent is preferably 20:1 to 100:1.

27. A method of claim 23, wherein said polymeric backbone is a polyamino acid having 20 to 560 amino acid residues.

28. A method of claim 27, wherein said polyamino acid is poly-1-lysine.

29. A method of claim 23, wherein said protective groups comprise from 17 to 220 ($OCH_2CH_2$) groups.

30. A method of claim 23, wherein said protective group is a polyethylene glycol derivative.

31. A method of claim 30, wherein said derivative is a methoxypolyalkylene glycol.

32. A method of claim 23, wherein said chelating group is a compound which binds cations of transitional elements and lanthanides.

33. A method of claim 32, wherein the chelating group is a compound which binds cations of technetium.

34. A method of claim 33, wherein the chelating group is a compound which binds 99 mTc pertechnetate.

35. A method of claim 33, wherein the chelating group is a compound which binds cations of indium.

36. A method of claim 33, wherein said chelating group is selected from the group consisting of diethylenetriaminepentaacetic acid monoamide, mercaptoacetyltriglycine monoamide, ethylenedicysteine monoamide, 1-imine-4-mercaptobutane, and bis (aminoethanethiol) carboxylic acid monoamide.

37. A method of claim 23, wherein said reducing agent is stannous (II) chloride or sodium dithionite.

38. A method of claim 23, wherein said buffer comprises sodium acetate.

39. A method of claim 23, wherein said imaging agent is a compound having the formula:

wherein the groups can be linked in any order, e.g., the $R_1$ unit can be repeated several times in the chain before an $R_2$ unit occurs, and vice versa; wherein k is 10–560; $R_1$ is $(CH_2)_4NHCO(CH_2)_nCOOCH_2CH_2A$—B—$OR_3$ where n=0–8, $R_3$=H, $(CH_2)_pCH_3$ or $(CH_2)_pCOOH$, where p=0–7, A=$[OCH_2CH_2]_x$, where x is 15–220, and B=$[OCH_2CH_2]_x$ or $[OCH(CH_3)CH_2]_y$, where y+x is 10–220; and $R_2$ is $(CH_2)_4$—$R_4$, where $R_4$ is a chelating group.

40. A method of claim 23, wherein said radioactive isotope is a technetium isotope.

41. A method of claim 40, wherein said isotope is 99 mTc pertechnetate.

42. A method of claim 23, wherein the blood pool imaging composition is provided in the form of a solution.

43. A method of claim 23, wherein the blood pool imaging composition is provided in the form of a freeze-dried powder.

44. A method of claim 23, further comprising the step of imaging a predetermined area of the patient's body with a gamma camera after introduction of the blood pool imaging composition into the patient's bloodstream.

* * * * *